US010172980B2

(12) United States Patent  (10) Patent No.: US 10,172,980 B2
Granada et al.  (45) Date of Patent: Jan. 8, 2019

(54) TISSUE SEPARATION BARRIER SYSTEMS AND RELATED METHODS OF USE

(71) Applicants: David Enrique Jiménez Granada, Dover, NH (US); Alejandro Gómez Rodríguez, Medellín (CO)

(72) Inventors: David Enrique Jiménez Granada, Dover, NH (US); Alejandro Gómez Rodríguez, Medellín (CO)

(73) Assignee: DME3D S.A.S., Medellin (CO)

( * ) Notice: Subject to any disclaimer, the term of this patent is extended or adjusted under 35 U.S.C. 154(b) by 0 days.

(21) Appl. No.: 15/382,665

(22) Filed: Dec. 17, 2016

(65) Prior Publication Data
US 2017/0173224 A1    Jun. 22, 2017

Related U.S. Application Data

(60) Provisional application No. 62/268,610, filed on Dec. 17, 2015.

(51) Int. Cl.
*A61L 31/12* (2006.01)
*A61L 31/06* (2006.01)
(Continued)

(52) U.S. Cl.
CPC ............ *A61L 31/128* (2013.01); *A61L 31/06* (2013.01); *B29B 7/90* (2013.01); *B29C 45/0001* (2013.01); *B29C 45/40* (2013.01); *B29C 45/7207* (2013.01); *C08G 77/04* (2013.01); *C08G 77/06* (2013.01); *B29K 2083/00* (2013.01); *B29K 2105/16* (2013.01); *B29K 2509/02* (2013.01); *B29L 2031/7546* (2013.01); *C08G 77/12* (2013.01); *C08G 77/20* (2013.01); *C08G 2120/00* (2013.01); *C08K 3/36* (2013.01);
(Continued)

(58) Field of Classification Search
CPC ........ C08L 83/04; C08L 83/00; A61L 31/128; A61L 31/06; C08K 3/36; C08K 5/56; B29B 7/90; B29C 45/0001; B29C 45/40; B29C 45/7207; B29K 2083/00; B29K 2105/16; B29K 2509/02; B29L 2031/7546
See application file for complete search history.

(56) References Cited

U.S. PATENT DOCUMENTS 5,795,584 A     8/1998  Totakura et al.
5,919,476 A *   7/1999  Fischer .................. A61L 15/26
                                                        424/443
(Continued)

OTHER PUBLICATIONS

Lee et al., Biomaterials 26 (2005) 671-678.*
(Continued)

*Primary Examiner* — Aradhana Sasan
(74) *Attorney, Agent, or Firm* — JWIP & Patent Services, LLC; Jason G. Weintraub, Esq.

(57) ABSTRACT

The present invention is directed to a tissue separation barrier system for preventing the abnormal union of two or more tissues, as well as related methods of use. These tissue separation barrier systems offer the balance of strength and flexibility to allow the tissues, such as skin, to move in a smooth and natural manner while affording a barrier between two or more tissues. Furthermore, particular embodiments of the present invention include the methods of manufacturing the tissue separation barrier systems of the present invention.

20 Claims, 3 Drawing Sheets

(51) Int. Cl.

| | |
|---|---|
| *B29C 45/72* | (2006.01) |
| *B29C 45/40* | (2006.01) |
| *B29C 45/00* | (2006.01) |
| *B29B 7/90* | (2006.01) |
| *C08G 77/04* | (2006.01) |
| *C08G 77/06* | (2006.01) |
| *C08G 77/12* | (2006.01) |
| *C08G 77/20* | (2006.01) |
| *C08K 5/56* | (2006.01) |
| *C08K 3/36* | (2006.01) |
| *C08L 83/00* | (2006.01) |
| *C08L 83/04* | (2006.01) |
| *B29K 83/00* | (2006.01) |
| *B29K 105/16* | (2006.01) |
| *B29K 509/02* | (2006.01) |
| *B29L 31/00* | (2006.01) |

(52) U.S. Cl.
CPC ............. *C08K 5/56* (2013.01); *C08L 83/00* (2013.01); *C08L 83/04* (2013.01)

(56) References Cited

U.S. PATENT DOCUMENTS

| | | |
|---|---|---|
| 2009/0048684 A1 | 2/2009 | Lesh |
| 2010/0174328 A1 | 7/2010 | Seaton et al. |
| 2011/0224341 A1 | 9/2011 | Davies et al. |
| 2011/0230810 A1 | 9/2011 | Raman et al. |

OTHER PUBLICATIONS

Bulters, D., et al., "Placement of silicone sheeting at decompressive craniectomy to prevent adhesions at cranioplasty," 2010, British J. Neurosurgery, 24(1):75-76.

Lee, C., et al., "Usefulness of silicone elastomer sheet as another option of adhesion preventive material during craniectomies," 2007, Clin. Neurology Neurosurgery, 109:667-671.

Lipshutz, H., et al., "The use of silicone rubber in the immediate reconstruction of fractures of the floor of the orbit," 1963, J. Trauma-Injury Infection Critical Care, 3(6):563-568.

\* cited by examiner

TISSUE SEPARATION BARRIER SYSTEMS AND RELATED METHODS OF USE

RELATED APPLICATIONS

This application claims priority to U.S. Provisional Patent Application No. 62/268,610, filed on Dec. 17, 2015; the entirety of which is incorporated herein by reference.

BACKGROUND OF THE INVENTION

A common complication of many different types of surgery is the formation of adhesions, otherwise known as adherences. Adhesions are considered abnormal fibrous tissue entities which form between tissues, thus abnormally adhering tissues to one another, particularly those tissues damaged from and/or during surgery. In fact, in some instances, additional surgery or surgeries are necessary to separate these joined tissues. Moreover, adhesions make any repeat surgeries difficult and hazardous to the subject.

Certain imperfect solutions currently exist for external wound protection, yet do not offer a suitable solution to prevent the formation of these adhesions between tissues. However, the films, gels, and multi-tier products useful for wound protection lack true anti-adhesion properties. In reality, most of these wound protection solutions relate to materials which adhere to tissues and can become an integral part of the adhesions. Removal of these materials is difficult and may simply continue the cycle of tissue damage, adhesion formation, and surgery to remedy the adhesions. Moreover, these products, which may offer strength, do not offer the combined flexibility necessary for use internally Accordingly, there remains a need for implantable systems that are useful for tissue separation that are capable of serving as a barrier with sufficient strength, flexibility and reduced adhesion properties to allow for ease of implantation, prevention of adhesions, and ease of removal without tissue damage.

SUMMARY OF THE INVENTION

Accordingly, the present invention is directed to a tissue separation barrier system for preventing the abnormal union of two or more tissues, as well as related methods of use. These tissue separation barrier systems offer a balance of strength and flexibility to allow the tissues, such as skin and the subdermal tissues, to move in a smooth and natural manner while affording a barrier between two or more tissues. Furthermore, particular embodiments of the present invention include the methods of manufacturing the tissue separation barrier systems of the present invention.

As such, one aspect of the present invention provides a tissue separation barrier system for preventing the abnormal union of two or more tissues. The tissue separation barrier comprises a single layer anti-adhesion silicone polymer wherein the single layer anti-adhesion silicone polymer is engineered to be implantable between two or more tissues and with sufficient flexibility to allow for ease of movement of said tissues.

In another aspect, the present invention provides a reinforced silicone flex (RSF) composite, wherein said RSF composite is a two part composite system formed by the curing of a homogenized mixture of a Part A siloxane with a Part B siloxane and about 20% reinforcing material, e.g., silica. The Part A siloxane comprises reinforced dimethyl methylvinyl siloxane, and the Part B siloxane comprises reinforced dimethyl methylhydrogen siloxane.

In yet another aspect, the present invention provides a method of separating two or more tissues. The method comprises the implantation of a single layer anti-adhesion silicone polymer of any tissue separation barrier system of the present invention between two or more tissues. The single layer anti-adhesion silicone polymer is engineered with sufficient flexibility to allow for ease of movement of said tissues, such that said tissues remain separated until removal of said single layer anti-adhesion silicone polymer.

Another aspect of the present invention provides a method of preventing the abnormal union of any two or more tissues. The method comprises implantation of a single layer anti-adhesion silicone polymer of any tissue separation barrier system of the present invention between two or more tissues. The single layer anti-adhesion silicone polymer is engineered with sufficient flexibility to allow for ease of movement of said tissues, such that the abnormal union of said tissues is prevented until removal of said single layer anti-adhesion silicone polymer.

Another aspect of the present invention provides a method of protecting a sub-epidermal wound comprising implantation of a single layer anti-adhesion silicone polymer any tissue separation barrier system of the present invention between two or more tissues, wherein at least one of said tissues requires protection as a result of a wound, wherein said single layer anti-adhesion silicone polymer is engineered with sufficient flexibility to allow for ease of movement of said tissues, such that said sub-epidermal wound remains protected until removal of said single layer anti-adhesion silicone polymer.

An additional aspect of the present invention provides a method of manufacturing a single layer anti-adhesion silicone polymer of any tissue separation barrier system of the present invention. The method comprises the steps of: placing a mixture of a Part A siloxane and a Part B siloxane into a container, e.g., a cartridge, wherein the Part A siloxane comprises reinforced dimethyl methylvinyl siloxane, and the Part B siloxane comprises reinforced dimethyl methylhydrogen siloxane, and combined comprise about 20% reinforcing material, e.g., silica; subjecting the mixture to a pre-injection homogenization process: injecting the pre-injection processed mixture into a mold; curing the molded mixture in an oven; cooling the molded mixture to room temperature; and demolding the cured mixture, thus forming a single layer anti-adhesion silicone polymer of any tissue separation barrier system of the present invention.

Another aspect of the present invention provides any tissue separation barrier system of the present invention manufactured according to any method of manufacturing of the present invention.

BRIEF DESCRIPTION OF THE DRAWINGS

Advantages of the present apparatus will be apparent from the following detailed description, which description should be considered in combination with the accompanying drawings, which are not intended to limit the scope of the invention in any way.

DETAILED DESCRIPTION OF THE INVENTION

The present invention is directed to a tissue separation barrier system for preventing the abnormal union of two or more tissues, as well as related methods of use. The tissue separation barrier systems of the present invention comprise single layer anti-adhesion silicone polymers which offer a balance of strength and flexibility to allow the tissues, such as skin and the subdermal tissues, to move in a smooth and natural manner while affording a barrier between the two or more tissues.

Silicones, or siloxanes, which have had a long and complex history of use in the medical field, have found use as scaffolds or supports for tissue growth, and paradoxically have also been used to manufacture "inert" forms and shapes, such as surgically-implantable facial or breast implants. Such inert silicone implants are far from perfect in that these forms often require periodic removal and replacement. In some instances, particularly with relatively inflexible facial implants, skin may actually slip from and expose the implant.

The single layer anti-adhesion silicone polymers of the present invention are engineered to be implantable between two or more tissues and with sufficient flexibility to allow for ease of movement of said tissues. The ease of movement of said tissues relates to the increased ease of movement with respect to non-flexible alternative materials known in the art for external wound protection. As such, the tissue separation barrier systems of the present invention not only reduce possible complications in dozens of different types of surgical procedures, but it will also effectively reduce surgical times and in surgery consumptions, improving the efficiency of the surgical services. In certain embodiments, the tissue separation barrier systems afford comparatively less bleeding, and less risks of infection than would otherwise occur.

The present invention, including tissue separation barrier systems and related methods will be described with reference to the following definitions that, for convenience, are set forth below. Unless otherwise specified, the below terms used herein are defined as follows:

1. Definitions

As used herein, the term "a," "an," "the" and similar terms used in the context of the present invention (especially in the context of the claims) are to be construed to cover both the singular and plural unless otherwise indicated herein or clearly contradicted by the context.

The term "abnormal union" is used herein to refer to a sticking together of substances which are not normally connected, joined or adhered to or with one another. In the context of the present invention, the substances are tissues which are not normally connected, joined or adhered to or with one another. The abnormal union of tissues, e.g., adhesions, often occurs when damage to one or more tissues initiates an inflammatory process in which the tissues, e.g., damaged tissues, form a new, fibrous tissue which connects, joins or adheres the tissues, e.g., damaged tissues. Abnormal unions of tissue may occur between two or more damaged or undamaged tissues, or any combination thereof, e.g., a damaged tissue may abnormally unite with an undamaged tissue.

The term "about" is used herein in reference to the degree or extent of the term which it modifies, and that such extent is near but not exactly 100%, and industry accepted standards will assist in defining the quantitative aspects of how "near" 100% is defined. In certain embodiment, the term "about" may indicate a variability of ±1% surrounding the designated value.

The term "adhesion" is art recognized and is used herein to describe the new, fibrous tissue that abnormally unites one or more tissues which are not normally connected, joined or adhered to or with one another. Adhesions are often formed when damage to one or more tissues initiates an inflammatory process in which tissue, e.g., damaged tissues, form a new fibrous tissue which connects or joins tissues, e.g., damaged tissues. Adhesions may form between any two or more tissues of the same type, e.g., two normally spatially-distinct intestinal tissues may be joined by an adhesion following abdominal injury or surgery, or of different types, e.g., adhesions may join a bladder to an intestine after a hysterectomy. Adhesions may form between two or more damaged or undamaged tissues, or any combination thereof, e.g., a damaged tissue may form an adhesion with an undamaged tissue.

The term "anti-adhesion" is used hereinto describe the feature or ability of a material or substance to prevent the abnormal union of one or more tissues, e.g., damaged tissues. In certain embodiments, an anti-adhesion material or substance may operate by means of a physical barrier. The anti-adhesion materials of the present invention are comprised of a silicone polymer, e.g., a single layer silicone polymer.

The term "barrier" is used herein to describe a material or substance, e.g., a silicone polymer, which blocks, prevents, or hinders the abnormal union of tissues, e.g., damaged tissues.

The term "C1-3alkyl" is art recognized and used to describe lower linear or branched carbon chain functional groups on a molecular structure, including but are not limited to, for example, methyl, ethyl, propyl, or isopropyl.

The terms "comfort" or "comfortable" are used herein to describe the feature or ability of a material or substance to ease pain or constraint, or to prevent a physically unpleasant feeling to a user/subject, i.e., when implanted between two or more tissues, or otherwise associated to or with the user, the comfort of the materials described herein as useful in the tissue separation barriers of the present invention produce less of, e.g., do not produce, a feeling of physical discomfort based on the underlying flexibility engineered into the material.

The term "damage" as used herein with respect to tissues, is used herein to describe any injury or harm to a cell, tissue, organ, or subject. The damage may be visible to the naked eye, such as an incision in the skin, or may be invisible to the naked eye, such as damage to individual cells at the site of an incision or wound.

The term "encircle" is art recognized, and is used herein to describe the feature and ability of a material or substance (e.g., a single layer silicone polymer tissue separation barrier system of the present invention) to form a partial or complete circle around an object, e.g., a tissue or an organ in need of a protective barrier to prevent the formation of adhesions following surgery.

The terms "flexible" or "flexibility" are used herein to describe the fluidity or lack of stiffness of a material or substance, e.g., a silicone polymer. A flexible material is one that is supple, and can be easily folded, rolled, bent, draped, crushed, or the like. In particular, the silicone polymers useful in the present invention are sufficiently supple and flexible to allow for sufficient ease of movement of tissues when worn, used or otherwise associated to or with a user/subject. In certain embodiments, this sufficient flexibility affords enhanced comfort control.

The term "force" is art recognized, and used herein to describe the push, pull or torsion upon an object resulting from the object's interaction with another object. The force may be actively applied to the objects, for example, during implantation tissue is moved or "forced" in place relative to a single layer silicone polymer tissue separation barrier system of the present invention; or, for example, a user rubs, touches, twists, or otherwise moves or "forces" a tissue relative to an implanted single layer silicone polymer tissue separation barrier system of the present invention. The force also may be passively applied to the objects, for example gravity is a force which, given ample time, causes motion or a change of position of one object to another.

The term "homogenize" is art recognized, and used herein to describe the blending or disbursement of elements of a mixture into a uniform mixture. A mixture that is homogenized is often said to be "homogenous"; the components of the mixture are substantially uniformly and evenly distributed.

The language "in need of" is art recognized to describe a property where a pre-condition or diagnosis suggests that the subject or situation would be benefited.

The term "organ" is art recognized and is used herein to describe a part of a body, e.g., a mammalian body, that has a differentiated structure consisting of cells and tissues which function and/or cooperate in a coordinated manner to perform some specific function in an organism, e.g., a heart or a kidney.

The language "reinforcing material" is art recognized with respect to siloxane polymers to describe the material/composition that may be added during or before the formation of the polymer to alter the properties of the ultimate polymeric form, e.g., related to strength and flexibility. For example, the term "reinforced dimethyl methylvinyl siloxane" is used herein to describe dimethyl methylvinyl siloxane with reinforcing material added into the component, e.g., silica, e.g., fumed silica.

The term "silica" is art recognized to describe silicon dioxide, (i.e., $SiO_2$). Silica may exist in crystalline or amorphous forms. "Fumed silica," is an amorphous silica that have been fused, e.g., fused in a flame or fire; and it exhibits a high surface area and extremely low bulk density which impart viscosity-increasing, time-dependent shear thinning properties. Fumed silica powder is used as a thickener or reinforcing filler in the manufacture of materials of the present invention, e.g., a single layer silicone polymers used in the tissue separation barrier systems of the present invention.

The terms "silicone" and "siloxane" are art recognized and used interchangeable herein to describe a compound having a molecular structure based on a chain of alternate silicon and oxygen atoms with organic groups (e.g., methyl, ethyl, propyl, vinyl, and phenyl) attached to the silicon atoms. The polymers of silicone are generally described by their monomeric units which may be incorporated by combination thereof, e.g., catalytic combination. The resulting polymers of silicone may afford a variety of properties, which may be modified by the addition of additives or reinforcing material during the combination process.

The term "single layer" is used herein to describe a homogenous material or substance of any depth, thickness, height, width or shape, e.g., independent of initial or final shape. A single layer of material or substance is of the same composition on the interior as on any outside surface of the material.

The terms "subject" and "patient" refer to an animal (e.g., a bird such as a chicken, quail or turkey) or a mammal including non-primates (e.g., a cow, pig, horse, sheep, rabbit, guinea pig, rat, cat, dog, and mouse) and primates (e.g., a monkey, chimpanzee and a human). In a particular embodiment, the subject is a human. A subject may or may not be experiencing a disease, disorder, wound or other ailment. In certain embodiments, the subject is a subject in need of treatment with the tissue separation barrier systems of the present invention based on a prior understanding of the presence of the disease, disorder, wound or other ailment.

The term "tissue" is art recognized and is used herein to describe a group or aggregate of cells and their surrounding intercellular substances that form a structure or structural material within a subject. The cells may be classified as a particular kind or type of cell, for example, connective tissue, epithelium, muscle tissue, or nerve tissue, and the like.

The term "wound" is art recognized, and is used herein to describe a physical injury to a body, e.g., a mammal, by which an opening, laceration or break is made to living tissue. The wound may be epidermal, e.g., a wound to the skin or sub-epidermal, e.g., a wound to the membrane covering a kidney. In certain embodiments, for example, the physical injury resulting in a wound may be from violence, an accident or from a surgery.

II. Tissue Separation Barrier Systems of the Invention

One embodiment of the present invention provides a tissue separation barrier system for preventing the abnormal union of two or more tissues comprising a single layer anti-adhesion silicone polymer wherein the single layer anti-adhesion silicone polymer is engineered to be implantable between two or more tissues and with sufficient flexibility to allow for ease of movement of said tissues. In certain embodiments the tissue separation barrier system may further comprise additional components selected from the group consisting of instructions, packaging, a coloring additive, a radiopacity additive (e.g., barium), an embedded sensor for communication of information from the implanted single layer anti-adhesion silicone polymer (e.g., for communicating pressure, temperature, or electrical signal at the implanted single layer anti-adhesion silicone polymer), a digital marker (e.g., micro-transponder, such as digital marker for RFID), NFC technology, an antibiotic, and any combination thereof, i.e., without affecting the ability of the tissue separation barrier system to perform its intended function. In certain embodiments, the tissue separation barrier system may further comprise a coating, such as, an antibiotic coating or an active coating, e.g., color changing coating in the presence of certain antigens or similar reactions, without affecting the ability of the tissue separation barrier system to perform its intended function. In particular embodiments, the tissue separation barrier system comprises one or more antibiotics dispersed within the single layer anti-adhesion silicone polymer, without affecting the ability of the tissue separation barrier system to perform its intended function. In certain embodiments, the tissue separation barrier system may further comprise minimum invasive delivery technology.

In certain embodiments of the present invention, the single layer anti-adhesion silicone polymer is engineered to be implantable between two or more tissues in a subject, e.g., a human or animal. In particular embodiments, the single layer anti-adhesion silicone polymer is engineered for enhanced comfort control. The enhanced comfort control may be engineered into the single layer silicone polymer tissue separation barrier systems of the present invention to afford a substantial reduction in the physical discomfort possible, e.g., a reduction in the physically unpleasant feeling. It is the sufficient flexibility of these materials that allow for the sufficient ease of movement of tissues such that, when worn, used or otherwise associated to or with a user, the material affords/controls comfort in an enhanced manner, e.g., produces less of or does not produce a feeling of physical discomfort, and is thus comfortable, e.g., relatively comfortable, to a user/subject.

In certain embodiments of the present invention, the movement of said tissues is caused by the application of force on said tissues (e.g., external or internal pressure or torsion). Moreover, the engineered flexibility of the system, e.g., single layer anti-adhesion silicone polymer, affords the system the unique ability to sufficiently adjust to the application of force.

In certain embodiments of the present invention, the anti-adhesion silicone polymer comprises a reinforced silicone flex (RSF) composite, wherein said RSF composite is a two part composite system formed by the curing of a homogenized mixture of a Part A siloxane with a Part B siloxane and about 20% reinforcing material, e.g., silica; and wherein:

Part A siloxane comprises reinforced dimethyl methylvinyl siloxane, and

Part B siloxane comprises reinforced dimethyl methylhydrogen siloxane.

In certain embodiments, Part A and Part B are combined in a ratio of about 10 to 13 of Part A siloxane to 1 Part B siloxane in a weight/weight ratio to form the RSF composite. In particular embodiments, Part A and Part B are combined in a ratio of about 11.5 Part A siloxane to 1 Part B siloxane in a weight/weight ratio to form the RSF composite. In specific embodiments, the reinforcing material is silica, e.g., fumed silica.

In certain embodiments of the present invention, the single layer anti-adhesion silicone polymer is engineered to be functionally characterized by exhibiting a hardness of about 27 to about 33 on Shore A durometer;

a tensile strength of greater than or equal to about 600 psi;

a tear strength of about 100 ppi;

an elongation limit of greater than or equal to about 350%; and a linear shrinkage of about 2%.

In certain embodiments of the present invention, the single layer anti-adhesion silicone polymer may be constructed (e.g., shapeable via mold, or transformable via shear or cutting processes) into any form. In particular embodiments, the shear or cutting process is performed during the manufacture, e.g., before packaging. In particular embodiments, the user, e.g., surgeon, may further engage in a shear or cutting process, e.g., during surgery, to better suit clinical need.

In particular embodiments, the shape of the single layer anti-adhesion silicone polymer is any three dimensional form of a size, shape and thickness sufficient to separate tissues. In a specific embodiment, the shape of the single layer anti-adhesion silicone polymer is a sheet having a thickness of at least about 0.3 mm. (e.g., at least about 0.4 mm, e.g., at least about 0.5 mm, e.g., at least about 0.6 mm, e.g., at least about 0.7 mm, e.g., at least about 0.8 mm, e.g., at least about 0.9 mm, e.g., at least about 1 mm)

In particular, the single layer anti-adhesion silicone polymer may be shaped through the molding process. Alternatively, the single layer anti-adhesion silicone polymer may be divided, trimmed, pared, penetrated or otherwise modified in shape by another object, e.g., a sharp object, e.g., through cutting.

In certain embodiments of the present invention, the single layer anti-adhesion silicone polymer may be constructed (e.g., shapeable via mold, or transformable via shear or cutting processes) into rectangular (e.g., square shapes), such as 12 cm×12 cm, 3 cm×6 cm, or 242 cm×24 cm, and in a variety of thicknesses (e.g., 0.5 mm to 1 mm), such that the single layer anti-adhesion silicone polymer achieves the intended functions as described herein. In particular embodiments, the shape is a square shape of 12 cm by 12 cm and 0.8 mm of thickness.

In certain embodiments of the present invention, the single layer anti-adhesion silicone polymer is engineered for the separation of tissue selected from the group consisting of connective tissue, muscle tissue, nervous tissue, epithelial tissue, and any combination thereof. For example, connective tissue may be selected from the group consisting of blood, bone, tendon, ligament, adipose, and areolar; muscle tissue may be selected from the group consisting of smooth (e.g., lining an organ), skeletal, and cardiac; nervous tissue may be selected from the group consisting of central (e.g., brain, spinal cord), and peripheral (e.g., cranial nerves, spinal nerves, motor neurons); and epithelial tissue may be selected from the group consisting of cells that cover the surface of an organ (e.g., skin, airway, reproductive tract, and inner lining of the digestive tract).

In certain embodiments of the present invention, the single layer anti-adhesion silicone polymer is removable (e.g., without damaging said separated tissues, without damaging tissues surrounding said separated tissues, inducing bleeding, forming adhesions, or other complications).

In certain embodiments of the present invention, the single layer anti-adhesion silicone polymer is suitable for permanent implantation. (e.g., implanted by any suitable mechanical or surgically acceptable method of securing an implant)

In certain embodiments of the present invention, the single layer anti-adhesion silicone polymer exhibits non-reactive biocompatibility, e.g., as determined by ISO standards (e.g., non-inflammatory and non-allergenic). The biocompatibility of a material or substance with a living organism, e.g., a mammal, may be measured by many parameters such as, but not limited to, cytotoxicity, acute or subacute toxicity, systemic or subsystemic toxicity, chronic toxicity, sensitization, irritation, intracutaneous reactivity, genotoxicity, hemocompatibility, carcinogenicity, allergenicity, immunogenicity, comfort, implantability, durability, leaching of components, and the like.

In certain embodiments of the present invention, the tissue separation barrier system is permanently implantable. In this way, the tissue separation barrier system materials remain strong and in good condition over a long period of time and are suitable for existing as placed between two or more tissues for a long period of time without significant deterioration or loss of properties for use as a single layer silicone polymer tissue separation barrier system of the present invention.

In certain embodiments of the present invention, the silicone polymer is opaque, not opaque, or translucent.

Another embodiment of the present invention provides a tissue separation barrier system of the present invention manufactured according to any method of manufacturing as described herein.

A. Reinforced Silicone Flex (RSF) Composite

Another embodiment of the present invention provides a reinforced silicone flex (RSF) composite, wherein said RSF composite is a two part composite system formed by the curing of a homogenized mixture of a Part A siloxane with a Part B siloxane and about 20% reinforcing material, e.g., silica; and wherein:

Part A siloxane comprises reinforced di(C1-3alkyl) (C1-3alkyl)vinyl siloxane, e.g., dimethyl methylvinyl siloxane, and Part B siloxane comprises reinforced di(C1-3alkyl) (C1-3alkyl)hydrogen siloxane, e.g., dimethyl methylhydrogen siloxane. This RSF composite serves as the anti-adhesion silicone polymer in certain embodiments of the systems of the invention.

In certain embodiments, part A and/or B may be modified with additional polymeric units that do not affect the ability of the material to perform its intended function. For example, in a particular embodiment, the Part B siloxane may comprise reinforced (C1-3alkyl) vinyl di(C1-3alkyl) (C1-3alkyl)hydrogen siloxane, e.g., methyl vinyl dimethyl methylhydrogen siloxane.

In yet another embodiment of the present invention provides a reinforced silicone flex (RSF) composite, wherein said RSF composite is a two part composite system formed by the curing of a homogenized mixture of a Part A siloxane with a Part B siloxane and about 20% reinforcing material, e.g., silica; and wherein:

Part A siloxane comprises reinforced dimethyl methylvinyl siloxane, and

Part B siloxane comprises reinforced dimethyl methylhydrogen siloxane.

This RSF composite serves as the anti-adhesion silicone polymer in certain embodiments of the systems of the invention.

In certain embodiments of the present invention, the Part A and Part B are combined in a ratio of about 10 to 13 of Part A siloxane to 1 Part B siloxane in a weight/weight ratio to form the RSF composite. In particular embodiments, Part A siloxane and Part B siloxane are combined in a ratio of about 11.5 Part A siloxane to 1 Part B siloxane in a weight/weight ratio to form the RSF composite.

In certain embodiments of the present invention, the reinforcing material is silica, e.g., fumed silica.

The types and ratios of silicon monomers, i.e., siloxanes, along with the reinforcing material components may be adjusted to manipulate the properties of the composite (e.g., the softness, hardness, flexibility, biocompatibility, inertness, lifespan, leachability, elastic properties, and durability, and the like) solely to produce composites with the parameters described herein for the intended purposes described herein.

In certain embodiments of the present invention, the RSF exhibits a low transparency.

III. Method of Use of Tissue Separation Barrier Systems of the Invention

Another embodiment of the present invention provides a method of preventing the abnormal union of any two or more tissues comprising implantation of a single layer anti-adhesion silicone polymer of the tissue separation barrier systems of the present invention between two or more tissues, wherein said single layer anti-adhesion silicone polymer is engineered with sufficient flexibility to allow for ease of movement of said tissues, such that the abnormal union of said tissues is prevented until removal of said single layer anti-adhesion silicone polymer. In particular, in this embodiment, the tissue separation barrier system is used to prevent the abnormal union of two or more tissues, e.g., the formation of adhesions, by implantation in a manner that keeps the two or more tissues from being physically connected.

An additional embodiment of the present invention provides a method of separating two or more tissues comprising implantation of a single layer anti-adhesion silicone polymer of the tissue separation barrier systems of the present invention between two or more tissues, wherein said single layer anti-adhesion silicone polymer is engineered with sufficient flexibility to allow for ease of movement of said tissues, such that said tissues remain separated until removal of said single layer anti-adhesion silicone polymer. In particular, in this embodiment, the tissue separation barrier system is used as physical spacer unit to keep two or more distinct masses of tissues in separate spaces, i.e., not physically connected. While adhesion prevention may also occur, the tissue separation barrier systems are useful for their structural aspects as well.

In another embodiment, the present invention provides a method of protecting a sub-epidermal wound comprising implantation of a single layer anti-adhesion silicone polymer of the tissue separation barrier systems of the present invention between two or more tissues, wherein at least one of said tissues requires protection as a result of a wound, wherein said single layer anti-adhesion silicone polymer is engineered with sufficient flexibility to allow for ease of movement of said tissues, such that said sub-epidermal wound remains protected until removal of said single layer anti-adhesion silicone polymer. In particular embodiments, the implantation protects a sub-epidermal wound from tissues selected from the group consisting of connective tissue, muscle tissue, nervous tissue, epithelial tissue, and any combination thereof.

In certain embodiments of the methods of use of present invention, the method prevents the formation of adhesions between said tissues.

In certain embodiments of the methods of use of present invention, the tissues are in need of separation.

In certain embodiments of the methods of use of present invention, the tissues are in a subject, e.g., in a subject in need thereof.

In certain embodiments of the methods of use of present invention, the separated tissues are different types of tissues, e.g., where the method would prevent adhesions that might join a bladder to an intestine after a hysterectomy.

In certain embodiments of the methods of use of present invention, the separated tissues are of the same type of tissue, e.g., implanted within one type of tissue so that the same type of tissue is separated by the tissue separation barrier system, e.g., where two normally spatially-distinct intestinal tissues could be joined by an adhesion following abdominal injury or surgery.

In certain embodiments of the methods of use of present invention, at least one of said tissues surrounds part or all of an organ and said implanted single layer anti-adhesion silicone polymer partially or fully encircles said organ.

In certain embodiments of the methods of use of present invention, at least one of said tissues is the tissue of an organ.

In certain embodiments of the methods of use of present invention, the abnormal union is in need of being prevented, e.g., in need of remaining non-adhered to neighboring tissues, e.g., to achieve proper healing.

IV. Method of Manufacture of Tissue Separation Barrier Systems of the Invention Another embodiment of the present invention provides a method of manufacturing a single layer anti-adhesion silicone polymer of the present invention comprising the steps of:
placing a mixture of a Part A siloxane and a Part B siloxane into a container, e.g., a cartridge, wherein the Part A siloxane comprises reinforced dimethyl methylvinyl siloxane, and the Part B siloxane comprises reinforced dimethyl methylhydrogen siloxane, and combined comprise about 20% reinforcing material, e.g., silica;
subjecting the mixture to a pre-injection homogenization process;
injecting the pre-injection processed mixture into a mold;
curing the molded mixture in an oven (e.g., controlled oven, e.g., 40 to 150° C., e.g., 120° C.);
cooling the molded mixture to room temperature (e.g., 4-40° C., e.g., 15-25° C., e.g., 20° C.); and
demolding the cured mixture,
thus forming a single layer anti-adhesion silicone polymer of the tissue separation barrier system of the present invention.

In certain embodiments of the method of manufacturing of the present invention, the timing of the steps may be simultaneous where appropriate, e.g., pre-injection homogenization may occur when placing in the container.

In certain embodiments of the method of manufacturing of the present invention, the method further comprises subjecting the demolded cured mixture to a mechanical transformation process (e.g., cutting/shaping of the cured mixture, sterilization and/or non-damaging mechanical testing).

In certain embodiments of the method of manufacturing of the present invention, the Part A and Part B are combined in a weight/weight ratio of about 10 to 13 of Part A siloxane to 1 Part B siloxane. In particular embodiments of the method of manufacturing of the present invention, the Part A siloxane and the Part B siloxane are combined in a weight/weight ratio of about 11.5 Part A siloxane to 1 Part B siloxane.

In certain embodiments of the method of manufacturing of the present invention, the reinforcing material is silica, e.g., fumed silica.

In certain embodiments of the method of manufacturing of the present invention, the pre-injection homogenization process within the container, e.g., cartridge, comprises mechanical mixing, including for example, agitation or stirring. In certain embodiments, the pre-injection homogenization process within the container, e.g., cartridge, further comprises the step of degassing said mixture. In specific embodiments, the pre-injection homogenization process further includes contaminant inspection, e.g., visualization to ensure no particulate contaminant is present in the mix.

In certain embodiments of the method of manufacturing of the present invention, the oven temperatures range from about 40° C. to about 150° C. In a particular embodiment the oven temperature is about 120° C. In certain embodiments, the cure period may range from 30 minutes to an hour, e.g., 45 minutes.

In certain embodiments of the method of manufacturing of the present invention, the anti-adhesion silicone membrane is subjected to a sterilization process. In particular embodiments, the sterilization process is selected from the group consisting of autoclaving (e.g., autoclaving in an ISO certified methodology), exposure to ultraviolet light and chemical sterilization.

In certain embodiments of the method of manufacturing of the present invention, the method is performed in a controlled environment suitable for producing a sterile, contaminant-free and defect-free single layer anti-adhesion silicone polymer suitable for surgical use. In particular embodiments of the invention, the present invention provides a device that affords the controlled environment characterized by the properties selected from the group consisting of dried and filtered air quality used for injection, increased compactness as compared with existing devices, compatible with ISO 6 type clean room, a homogenization system included which is under vacuum and sterile, certified to not use any contaminant or pyrogenetic material that could damage humans if implanted or in contact with blood and tissue, and any combination thereof.

EXEMPLIFICATION

Having thus described the invention in general terms, reference will now be made to the accompanying figures and exemplary embodiments, which are not intended to be limiting in any way.

In this respect, it is to be understood that the invention is not limited in its application to the details of construction and to the arrangements of the components set forth in the following description or illustrated in the figures. The invention is capable of other embodiments and of being practiced and carried out in various ways. Also, it is to be understood that the phraseology and terminology employed herein are for the purpose of description and should not be regarded as limiting.

Example 1

Preparation of Reinforced Silicone Flex (RSF) Composite

The reinforced silicone flex (RSF) composite described herein, e.g., as useful in the tissue separation barrier systems of the present invention is a two part composite system formed by the curing of a homogenized mixture of a Part A siloxane with a Part B siloxane and about 20% reinforcing material. In one embodiment, the Part A siloxane comprises reinforced dimethyl methylvinyl siloxane (Applied Silicone Corporation, PN40029 Part A), and the Part B siloxane (Applied Silicone Corporation, PN40029 Part B) comprises reinforced dimethyl methylhydrogen siloxane.

Reinforced dimethyl methylvinyl siloxane (reinforced with about 20% fumed silica) was homogenized with reinforced dimethyl methylhydrogen siloxane (reinforced with about 19.8-20% fumed silica and comprising a catalytic amount of platinum suitable for catalytic hydrosilylation) at a ratio of 11.5 to 1 weight/weight in a controlled environment in a clean room ISO class 6. The pre-injection homogenized mixture, comprising about 20% reinforcing material, was then submitted to a mechanical treatment for complete homogenization, with extraction of air from the mix via degassing, followed by contaminant inspection.

The degassed mixture was then placed into a cartridge/container for use on an injection machine which injects the mix into a mold, all of which was done with the mix completely protected from the environment and only using sterilized and cleaned instruments with the support of air pressure with certified filtered air and the sterile and clean containers.

The injection process, which was supervised to avoid spills and contaminants, positioned the mixture inside a mold that was then cured at 120 degrees Celsius in a controlled oven for 45 minutes. The mold was then cooled at 20 degrees Celsius until the temperature was the same as the room, forming a single layer anti-adhesion silicone polymer. The single layer anti-adhesion silicone polymer was then demolded and checked for contaminants and physical imperfections that could affect the correct function of the material as used in the tissue separation barrier systems of the present invention as described herein.

The single layer anti-adhesion silicone polymer may be then cut into any shape depending on the specific use. Subsequently, a second supervision for contaminants and physical defects may then be performed.

The shaped material was then cleansed in a controlled environment, folded as necessary, and packed in a sterilization bag for sterilization in steam.

A final check for possible damage was performed, followed by packaging in a final package before being shipped to the operating room for use.

Implant tests used to assess the local effects of material on living tissue at both the macroscopic and microscopic levels according to ISO standards are shown in Examples 3, 4 and 5. Further, the use of the RSF composite in a tissue separation barrier system of the present invention is demonstrated in Example 2.

Example 2

Surgical Use of Tissue Separation Barrier System

A. Craniectomy with Bi-Coronal Incision of a Skin Flap

The single layer anti-adhesion silicone polymer of Example 1, as used as a tissue separation barrier system of the present invention, was used to protect one tissue from an adjacent one during a decompressive craniectomy over the open dura directly on the brain tissue.

In this respect, the tissue separation barrier system of the present invention was placed over the open dura directly on the brain tissue in the decompressive craniectomy.

Figure 1:
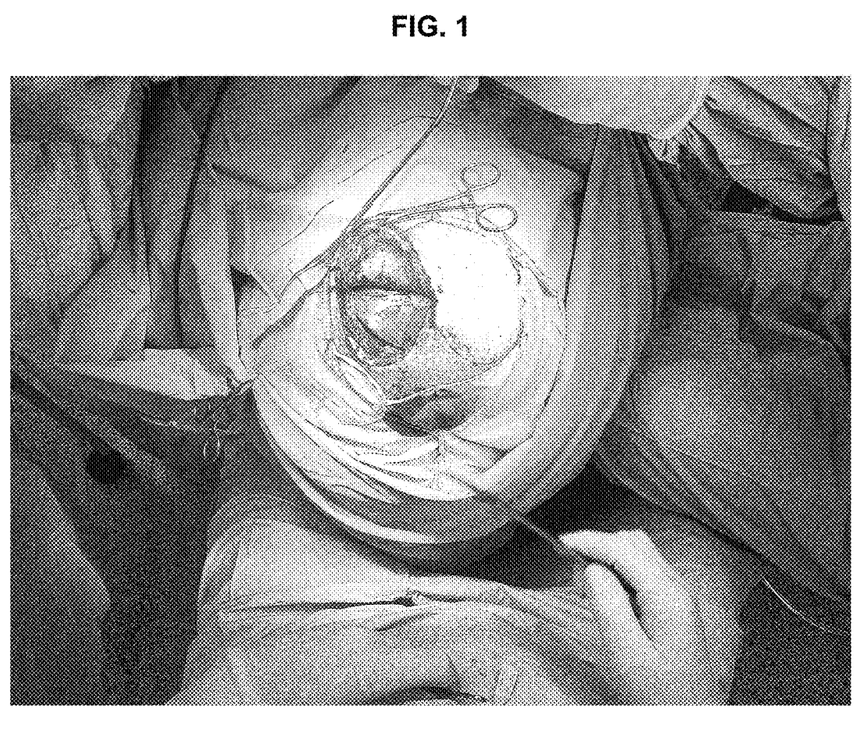
FIG. 1 is a photographic image that depicts a top down perspective view of the opening of an incision after a first surgical craniectomy, wherein the skin flap is observed as intact. One embodiment of the tissue separation barrier systems of the present invention may be seen inside the brain cavity, which allows the skin flap to be easily separated.

FIG. 1 is a photographic image that depicts a top down perspective view of the opening of an incision after a first surgical craniectomy, wherein the skin flap is observed as intact. The tissue separation barrier system of the present invention may be seen inside the brain cavity, which allows the skin flap to be easily separated, i.e., when the skin flap is closed the dermis will not adhere to either the single layer anti-adhesion silicone polymer or the tissue under it. As such, during the chronical reintervention of the cranioplasty, the skin flap will be separated from all the tissue, avoiding having to make the incisions to find the field between periosteum and dura or brain tissue. It reduced time (i.e., only 5 minutes was necessary for a bi-coronal incision of the skin flap), reduced bleeding, reduced risk of producing a CFR fistula and reduced similar risks related to the procedure of separating such tissues, and that way reducing the morbidity of the patient and increasing productivity of the surgery.

Figure 2:
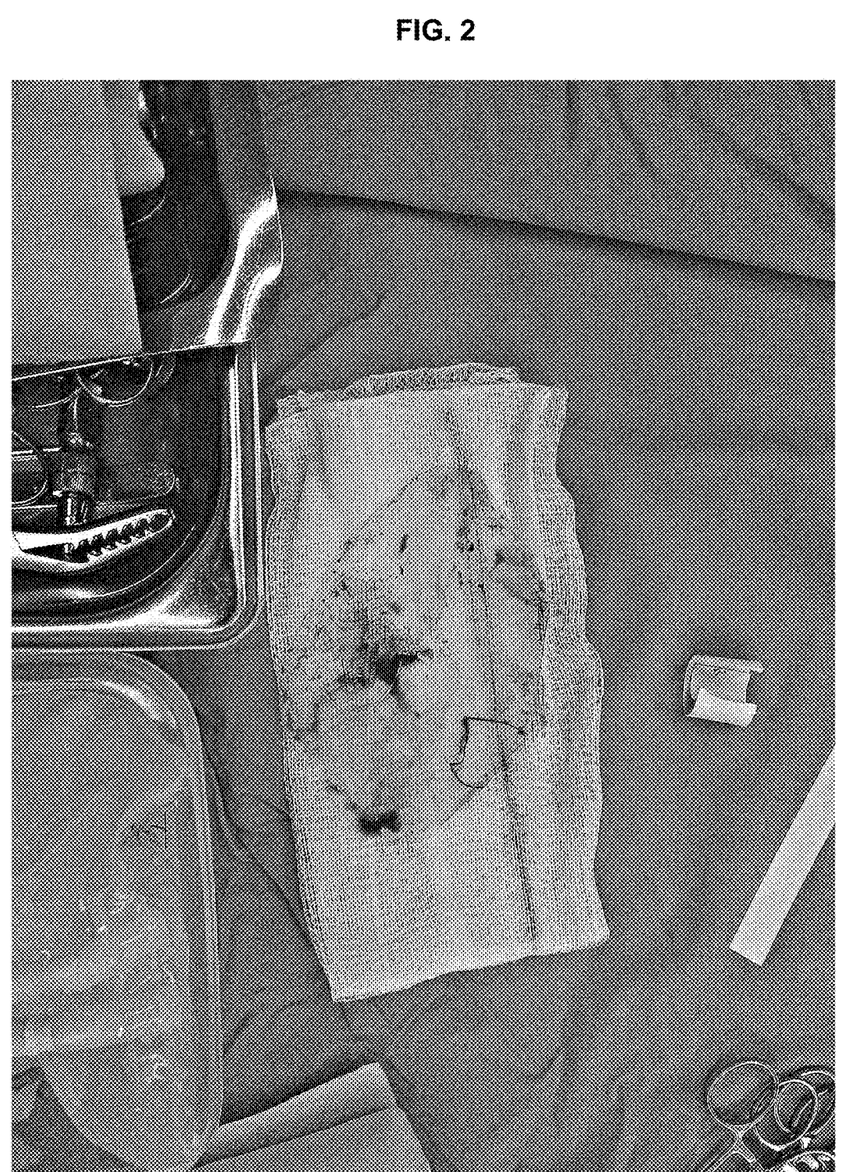
FIG. 2 is a photographic image that depicts the retrieved tissue separation barrier system seen in FIG. 1, which further shows no tissue adhered to it whatsoever.
Figure 3:
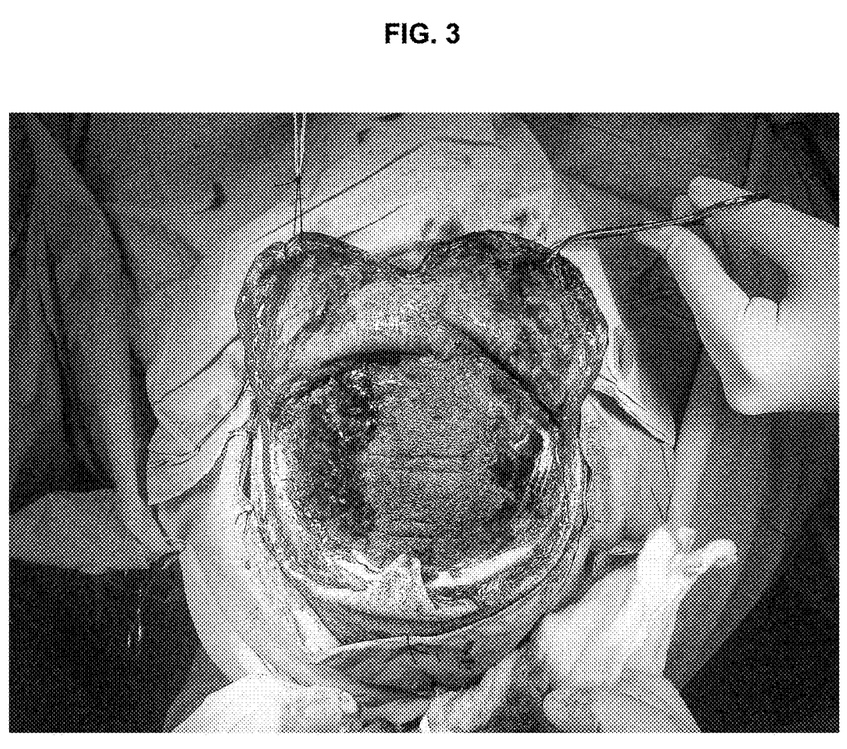
FIG. 3 is a photographic image that depicts the flap of FIG. 1 completely opened. It was achieved in a surprisingly fast manner, i.e., just 2 minutes, with no need to do any type of coagulation with a perfectly preserved periosteum in the skin flap (i.e., in known surgeries of similar nature the skin flap must be coagulated with a bipolar bayonet), and the bone margin is completely exposed.

Further, FIG. 2 is a photographic image that depicts the retrieved tissue separation barrier system seen in FIG. 1, which further shows no tissue adhered to it whatsoever. And FIG. 3 is a photographic image that depicts the flap of FIG. 1 completely opened. It was achieved in a surprisingly fast manner, i.e., just 2 minutes, with no need to do any type of coagulation with a perfectly preserved periosteum in the skin flap (i.e., in known surgeries of similar nature the skin flap must be coagulated with a bipolar bayonet), and the bone margin is completely exposed.

B. Additional Examples

Another example where the tissue separation barrier systems of the present invention would be similarly useful would be to protect surgical sites with aggressive fibrotic outcomes, e.g., to avoid adhesions between the organs, e.g., for life. For example, protections of the dura after a laminectomy or similar intervention, avoiding the fibrosis caused adherence to the medula's dura, for life. In fact, the device can be implanted for the duration of the life of the subject, without losing any of its characteristics.

In yet another example, the tissue separation barrier systems of the present invention would be similarly useful to position after making an eventration intervention with a mesh. The tissue separation barrier system may be placed over the intestines to avoid the adherence of them to the mesh, reducing the complications related with such adhesions.

Example 3

Cytotoxicity Analysis (ISO 10993-5)

The toxicity of the reinforced silicone flex (RSF) composite described herein and used in the tissue separation barrier systems of the present invention, was evaluated in vitro.

Materials and Supplies:

| Material/Supply | Lot number | Manufacturer |
| --- | --- | --- |
| Single Strength Minimum Essential Medium with Earle's Salts (1XMEM) | 1535328 | LIFE TECHNOLOGIES ® |
| Horse Serum | 61373986 | ATCC |
| Fungizone (amphotericin B solubilized) | 1392647 | LIFE TECHNOLOGIES ® |
| Penicillin-streptomycin | 1411482 | LIFE TECHNOLOGIES ® |
| Dulbecco's Phosphate Buffered Saline (PBS) | 61443818 | ATCC |

Multiple cultures of L-929 mammalian (mouse) fibroblast cells (ATCC cell line CCL 1, NCTC clone 929) were prepared according to methods known in the art. The cell were grown in 10 cm$^2$ wells in a 5% serum supplemented cell culture medium and incubated at 37±1° C. in a humidified incubator with 5±1% $CO_2$. The cell cultures were plated 24-48 hours prior to use in order to allow for a cell monolayer with greater than 80% confluence to form.

An extract of the reinforced silicone flex (RSF) composite described herein was prepared by incubating the RSF composite with Minimum Essential Medium (MEM). MEM was a 5% serum supplemented cell culture medium comprised of 93% single strength minimum essential medium with Earle's salts (1×MEM), 5% horse serum, 1% penicillin-streptomycin, and 1% fungizone (amphotericin B solubilized).

An ethylene-oxide sterilized sheet of RSF composite having a total surface area of 136.0 cm² was used for the extraction at a ratio of 60 cm²/20 ml (thickness was equal to or greater than 0.05 cm), yielding a volume of 45.3 mL. The sheet of RSF composite was cut into small pieces and placed in a sterile glass container. To prepare the test extract, MEM extraction medium was added and the pieces of RSF composite were completely immersed. In a similar fashion, control extracts lacking the RSF composite were also prepared; the negative control extract was prepared using an autoclave-sterilized USP high-density polyethylene reference standard plastic (USP) and the positive control extract was prepared using non-sterile Tygon AF4040 plastic (Saint-Gobain Performance Plastics). The test and control extract solutions were incubated for 24±2 hours at 37±1° C. with agitation. Tables 1 and 2 show the duration and conditions used to prepare the test and control extracts. Before extraction, all solutions appeared clear and free of particulates.

TABLE 1

Extraction of RSF composite

| Total surface area (cm²) | Extraction ratio (cm²/mL) | Total volume extracted (mL) | Extraction medium | Extraction Temperature (° C.) | Duration (hrs) |
|---|---|---|---|---|---|
| 136.0 | 60/20 | 45.3 | 1XMEM | 37 ± 1 | 24 ± 2 |

TABLE 2

Extraction of positive, negative, and reagent only controls

| Extract | Surface areas Area (cm²) | Extraction ratio (cm²/mL) | Total volume (mL) | Extraction medium | Extraction Temperature (° C.) | Duration (hrs) |
|---|---|---|---|---|---|---|
| Positive control | 31.2 | 60/20 | 10.4 | 1XMEM | 37 ± 1 | 24 ± 2 |
| Negative control | 33.8 | 60/20 | 11.3 | | | |
| Reagent control | NA | NA | 20 | | | |

NA = not applicable

Test Procedure

Following the extraction period, each solution was visually inspected. The RSF composite extract appeared slightly opaque and small, wispy particulates were observed in the solution; the color of the RSF composite extract did not change during the incubation period. Particulate matter was absent from all control extracts and the color of the control extracts did not change during the incubation period. The extractions were not diluted, filtered, and/or manipulated in any way prior to dosing and were applied to the cultured cells within 24 hours of the completion of the extraction process.

For each solution tested, the growth medium was decanted from three wells, each containing a monolayer of L-929 mouse fibroblast cells (ATCC Cell Line CCL1, NCTC Clone 929), and rinsed with 2 mL of 1× Dulbecco's PBS. Following removal of the PBS, 2 mL of the RSF composite test or control solutions were flooded onto the cells. The cells were incubated for 48±2 hours at 37±1° C. in a humidified incubator with 5±1% $CO_2$.

At 24 and 48±2 hours following dosing, the cells were examined under an inverted light microscope using 100× magnification. The conditions of the cell cultures were graded according to the criteria in Table 3. The average score for the triplicate test wells at the 48-hour point was used to determine the final cytotoxic response of the cells to the RSF composite and control extracts.

TABLE 3

Qualitative morphological criteria used to grade the cell cultures

| Grade | Reactivity | Description of criteria |
|---|---|---|
| 0 | None | Discrete intracytoplasmatic granules, no cell lysis, no reduction of cell growth |
| 1 | Slight | Not more than 20% of the cells are round, loosely attached and without intracytoplasmatic granules, or show changes in morphology; occasional lysed cells are present; only slight growth inhibition observed |
| 2 | Mild | Not more than 50% of the cells are round, devoid of intracytoplasmatic granules, no extensive cell lysis; not more than 50% growth inhibition observed |
| 3 | Moderate | Not more than 70% of the cell layers contain rounded cells or are lysed; cell layers not completely destroyed, but more than 50% growth inhibition observed |
| 4 | Severe | Nearly complete or complete destruction of the cell layers |

Results

Test results for the RSF composite, positive, negative, and reagent controls are presented in Table 4.

TABLE 4

Test Results

| Replicate number | Reactivity 24 hrs | Grade 24 hrs | Reactivity 48 hrs | Grade 48 hrs |
|---|---|---|---|---|
| RSF composite extract #1 | None | 0 | None | 0 |
| RSF composite extract #2 | None | 0 | None | 0 |
| RSF composite extract #3 | None | 0 | None | 0 |
| Controls | | | | |
| Positive #1 | Moderate | 3 | Severe | 4 |
| Positive #2 | Moderate | 3 | Severe | 4 |
| Positive #3 | Moderate | 3 | Severe | 4 |
| Negative #1 | None | 0 | None | 0 |
| Negative #2 | None | 0 | None | 0 |
| Negative #3 | None | 0 | None | 0 |
| Reagent #1 | None | 0 | None | 0 |
| Reagent #2 | None | 0 | None | 0 |
| Reagent #3 | None | 0 | None | 0 |

0 = none (no reactivity);
1 = slight reactivity;
2 = mild reactivity;
3 = moderate reactivity;
4 = severe reactivity.

ISO Standard Interpretation: Cytotoxicity is Attributed to an Extract Exhibiting a Score of Greater than 2.

Cells treated with the RSF composite extract exhibited a response grade of 0, that is, no reactivity was observed at the 24 and 48 hour time points. Cells treated with the negative and reagent control extracts also exhibited a response grade of 0, that is, no reactivity was observed at the 24 and 48 hour time points. Cells treated with positive control extract exhibited a response grade of 3, that is, the cells were moderately affected, at the 24 hour time point; the severity of the cellular reaction increased to a response grade of 4, that is, the cells were severely affected, at the 48 hour time point.

Based upon the results of these experiments, the reinforced silicone flex (RSF) composite described herein and used in the tissue separation barrier systems of the present invention, does not elicit cytotoxicity or a cytotoxic response, that is, the RSF composite described herein, and thus the tissue separation barrier systems of the present invention utilizing the RSF composite, can be considered to be non-cytotoxic.

Example 4

Acute Systemic Toxicity Test (ISO 10993-11)

The acute systemic toxicity of the reinforced silicone flex (RSF) composite described herein and used in the tissue separation barrier systems of the present invention, was evaluated in vivo.

Materials and Supplies:

| Reagents | Lot number | Manufacturer |
|---|---|---|
| 0.9% Sodium Chloride Injection, USP (SCI) | 38-041-JT | Hospira |
| Cottonseed Oil (OIL) | 1CH0076 | Spectrum |

Twenty young, albino, adult male CD-1 mice (Charles River, Hollister, Calif.; initial weight 17-21 grams) were used to evaluate the in vivo effect of an extract of RSF composite; five mice were used for each test or control group. The mice were housed in groups in polycarbonate cages in a controlled environment at a nominal temperature range of 20 to 26° C., a humidity range of 50±20%, and a light/dark cycle of 12 hours. The mice received fresh drinking water and Certified Laboratory Rodent Diet ad libitum. The mice were allowed to acclimate to the conditions for 5 days prior to use.

An extract of the reinforced silicone flex (RSF) composite described herein was prepared by incubating the RSF composite with either 0.9% sodium chloride injection USP (SCI) or cotton seed (OIL). Ethylene-oxide sterilized sheets of RSF composite, each having a total surface area of 136.0 cm$^2$, were used for the extractions at a ratio of 60 cm$^2$/20 ml (thickness was equal to or greater than 0.05 cm), yielding a volume of 45.3 mL. Each sheet of RSF composite was cut into small pieces and were completely immersed in the appropriate volume of either SCI or OIL. SCI and OIL control extracts lacking the RSF composite were also prepared. The test and control extract solutions were incubated for 1±0.1 hours in an oven at 121±2° C. with agitation.

Test Procedure

Following extraction, the extracts were allowed to cool enough to be handled, shaken well and decanted into sterile vessels. The RSF composite sheet and the RSF composite extract were visually inspected after extraction and compared to control solutions. The RSF composite extracted in SCI and OIL appeared to be unaffected by the extraction process, remaining clear, with no change in color and no visible particulates. The cooled, inspected SCI and OIL extracts were administered to the mice within 24 hours of extraction; the extracts were administered undiluted and were not filtered.

A total of twenty (20) mice were used in this test, 10 mice each to the SCI and OIL groups. The 10 animals were further divided into five RSF composite test and five control groups for the SCI and OIL treatments. Five test mice from the SCI group were each injected intravenously, via tail vein, with 50 mL/kg of the RSF composite SCI extract at a slow, steady rate (approximately 100 uL/sec). Five control mice were each injected intravenously, via tail vein, with 50 mL/kg of the corresponding SCI control. Five test mice from the OIL group were each injected intraperitoneally with 50 mL/kg of RSF composite OIL extract. Five control mice were each injected intraperitoneally with 50 mL/kg of the corresponding OIL control.

The animals were observed for signs of biological reactivity at several time points after administration of the extracts: a) immediately after dosing, b) 4 hours±15 minutes, c) 24±2 hours, d) 48±2 hours, and e) 72±2 hours. The biological parameters observed included, but were not limited to, changes in skin and fur, eyes and mucous membranes, respiratory, circulatory, autonomic and central nervous system, somatomotor activity, weight, and behavior patterns. The animals were weighed prior to dosing and at the 24, 48 and 72 hour time points.

Results

TABLE 5

| | Clinical observations | | | | |
|---|---|---|---|---|---|
| Group | Animal number | Immediately after dosing | 4 hours | 24 hours | 48 hours | 72 hours |
| SCI test | 1 | NBR | NBR | NBR | NBR | NBR |
| | 2 | NBR | NBR | NBR | NBR | NBR |
| | 3 | NBR | NBR | NBR | NBR | NBR |
| | 4 | NBR | NBR | NBR | NBR | NBR |
| | 5 | NBR | NBR | NBR | NBR | NBR |
| SCI control | 6 | NBR | NBR | NBR | NBR | NBR |
| | 7 | NBR | NBR | NBR | NBR | NBR |
| | 8 | NBR | NBR | NBR | NBR | NBR |
| | 9 | NBR | NBR | NBR | NBR | NBR |
| | 10 | NBR | NBR | NBR | NBR | NBR |
| OIL test | 11 | NBR | NBR | NBR | NBR | NBR |
| | 12 | NBR | NBR | NBR | NBR | NBR |
| | 13 | NBR | NBR | NBR | NBR | NBR |
| | 14 | NBR | NBR | NBR | NBR | NBR |
| | 15 | NBR | NBR | NBR | NBR | NBR |
| OIL control | 16 | NBR | NBR | NBR | NBR | NBR |
| | 17 | NBR | NBR | NBR | NBR | NBR |
| | 18 | NBR | NBR | NBR | NBR | NBR |
| | 19 | NBR | NBR | NBR | NBR | NBR |
| | 20 | NBR | NBR | NBR | NBR | NBR |

NBR = no biological reactivity

TABLE 6

| | Dose volumes and animal weights | | | | | |
|---|---|---|---|---|---|---|---|
| Group | Animal number | Dose (mL) | Pre-test weight (g) | 24 hr weight (g) | 48 hr weight (g) | 72 hr weight (g) | Weight change (g)* |
| SCI test | 1 | 1.0 | 20 | 21 | 22 | 25 | +5 |
| | 2 | 1.1 | 21 | 22 | 24 | 26 | +5 |
| | 3 | 1.0 | 19 | 21 | 23 | 26 | +7 |
| | 4 | 1.0 | 20 | 21 | 23 | 25 | +5 |
| | 5 | 1.0 | 20 | 23 | 25 | 27 | +7 |
| SCI control | 6 | 1.0 | 20 | 22 | 24 | 26 | +6 |
| | 7 | 1.0 | 19 | 21 | 23 | 24 | +5 |
| | 8 | 1.0 | 19 | 21 | 23 | 25 | +6 |
| | 9 | 1.0 | 20 | 21 | 22 | 24 | +4 |
| | 10 | 1.0 | 19 | 21 | 23 | 24 | +5 |
| OIL test | 11 | 1.0 | 19 | 21 | 22 | 24 | +5 |
| | 12 | 0.9 | 18 | 19 | 22 | 24 | +6 |
| | 13 | 0.9 | 18 | 21 | 23 | 24 | +6 |
| | 14 | 1.0 | 19 | 21 | 23 | 25 | +6 |
| | 15 | 0.9 | 18 | 20 | 21 | 23 | +5 |

TABLE 6-continued

Dose volumes and animal weights

| Group | Animal number | Dose (mL) | Pre-test weight (g) | 24 hr weight (g) | 48 hr weight (g) | 72 hr weight (g) | Weight change (g)* |
|---|---|---|---|---|---|---|---|
| OIL control | 16 | 1.0 | 19 | 21 | 22 | 24 | +5 |
| | 17 | 1.0 | 19 | 21 | 22 | 24 | +5 |
| | 18 | 0.9 | 18 | 19 | 21 | 23 | +5 |
| | 19 | 0.9 | 18 | 19 | 20 | 22 | +4 |
| | 20 | 0.9 | 17 | 18 | 20 | 21 | +4 |

*Body weight change was calculated by subtracting the pre-test weight from the 72 hour weight The biological observations are presented in Table 5, where it can be seen that all animals from all four SCI and OIL groups appeared healthy; no abnormalities were observed at any of the specified time points during the three day observation period. Exposure of the mice to the RSF composite extracts, both in SCI and OIL, did not result in observable symptoms of acute systemic toxicity.

The animal body weights and dose volumes are presented in Table 6. All of the animals in the SCI groups gained weight by the end of the test. The animals dosed with the RSF composite SCI extract gained about 5 to 7 grams while the animals dosed with the SCI control extract gained about 4 to 6 grams. The animals dosed with the RSF composite OIL extract gained about 5 to 6 grams while the animals dosed with the OIL control extract gained about 4 to 5 grams.

Example 5

Intracutaneous (Intradermal) Reactivity Test (ISO 10993-10)

The local response of the reinforced silicone flex (RSF) composite described herein and used in the tissue separation barrier systems of the present invention, was evaluated in vivo.

Materials and Supplies:

| Reagents | Lot number | Manufacturer |
|---|---|---|
| 0.9% Sodium Chloride Injection, USP (SCI) | 38-041-JT | Hospira |
| Cottonseed Oil (OIL) | 1CHD076 | Spectrum |

Three adult female New Zealand White rabbits (Western Oregon Rabbit Company, Philomath, Oreg.; initial weight 2.6-2.9 kgs) were used to evaluate the localized in vivo effect of an extract of the RSF composite; each rabbit was used for both test and control injections. The animals were housed individually in suspended cages and maintained in a controlled environment at a nominal temperature range of 16 to 22° C., a humidity range of 50±20%, and a light/dark cycle of 12 hours. The rabbits received a Certified Laboratory Rabbit Diet (approximately 165 grams per day) and water ad libitum. The animals were acclimated to the testing facility for at least 7 days prior to initiation of the study. Health observations were performed prior to the study to ensure that the animals were acceptable for study use.

An extract of the reinforced silicone flex (RSF) composite described herein was prepared by incubating the RSF composite with either 0.9% sodium chloride injection USP (SCI) or cotton seed (OIL). Ethylene-oxide sterilized sheets of RSF composite, each having a total surface area of 136.0 $cm^2$, were used for the extractions at a ratio of 60 $cm^2$/20 ml (thickness was equal to or greater than 0.05 cm), yielding a volume of 45.3 mL. Each sheet of RSF composite was cut into small pieces and were completely immersed in the appropriate volume of either SCI or OIL. SCI and OIL control extracts lacking the RSF composite were also prepared. The test and control extract solutions were incubated for 1±0.1 hours in an oven at 121±2° C. with agitation.

Test Procedure

Following extraction, the extracts were allowed to cool enough to be handled, shaken well and decanted into sterile vessels. The RSF composite sheet and the RSF composite extract were visually inspected after extraction and compared to control solutions. The RSF composite extracted in SCI and OIL appeared to be unaffected by the extraction process, remaining clear, with no change in color and no visible particulates. The cooled, inspected SCI and OIL extracts were administered to the rabbits within 24 hours of extraction; the extracts were administered undiluted and were not filtered.

Three animals were used in this study. On the day of the test, the fur on the back of each animal was clipped with electric clippers. Each extract was vigorously agitated prior to withdrawal of injection doses to ensure even distribution of extracted matter. A volume of 0.2 ml- of the RSF composite extract in SCI was injected intracutaneously at five sites on one side of the spinal column, anterior to the midline, of each of three rabbits. A 0.2 mL portion of SCI control was injected intracutaneously at five sites on the opposite side of the spinal column of the same three rabbits (FIG. 1). This process was repeated on the same animals for the RSF composite extracted in OIL and OIL control but posterior to the dorsal midline. The dose sites were marked with permanent marker in order to aid in the identification of dose site locations.

The rabbits were observed daily for signs of ill health. The animals were also observed for signs of tissue reactivity, such as erythema, eschar formation and edema, at several time points after administration of the extracts: a) immediately after dosing, b) 24±2 hours, c) 48±2 hours, and d) 72±2 hours (see Table 7 for grading criteria).

TABLE 7

Classification system for intracutaneous (intradermal) reactions

| | Score |
|---|---|
| Erythema and eschar formation | |
| No erythema | 0 |
| Very slight erythema (barely perceptible) | 1 |
| Well-defined erythema | 2 |
| Moderate to severe erythema | 3 |
| Severe erythema (beet-redness) to eschar formation preventing grading of erythema | 4 |
| Edema formation | |
| No edema | 0 |
| Very slight edema (barely perceptible) | 1 |
| Slight edema (edges of area well defined by definite raising) | 2 |
| Moderate edema (raised about 1 mm) | 3 |
| Severe edema (raised more than 1 mm and extending beyond area of 4 exposure) | 4 |
| Total Possible Score for Irritation | 8 |

Table adopted from ISO 10993-10 Biological Evaluation of Medical Devices - Test for Irritation and Skin Sensitization.

After the 72 hour time point, all erythema grades plus edema grades (24. 48 and 72 his) were totaled separately for the test sites and control sites for each individual animal. For each individual animal, each of the totals was divided by 15 (3 scoring time points×5 test and control injection sites). The overall mean scores for each test and corresponding control were calculated by adding the scores for all three animals and dividing by three (total number of animals). The final test score was obtained by subtracting the overall mean score of the control from the overall mean score of the test.

Results

TABLE 8

Reaction scores (SCI extract)

| | TEST SITES | | |
|---|---|---|---|
| | 24 ± 2 hrs | 48 ± 2 hrs | 72 ± 2 hrs |
| Animal ID: 63104 | | | |
| Erythema | 0 0 0 0 0 | 0 0 0 0 0 | 0 0 0 0 0 |
| Edema | 0 0 0 0 0 | 0 0 0 0 0 | 0 0 0 0 0 |
| Total reaction score/observation | 0 | 0 | 0 |
| Total mean* | | 0 | |
| Animal ID: 63045 | | | |
| Erythema | 0 0 0 0 0 | 0 0 0 0 0 | 0 0 0 0 0 |
| Edema | 0 0 0 0 0 | 0 0 0 0 0 | 0 0 0 0 0 |
| Total reaction score/observation | 0 | 0 | 0 |
| Total mean* | | 0 | |
| Animal ID: 63106 | | | |
| Erythema | 0 0 0 0 0 | 0 0 0 0 0 | 0 0 0 0 0 |
| Edema | 0 0 0 0 0 | 0 0 0 0 0 | 0 0 0 0 0 |
| Total reaction score/observation | 0 | 0 | 0 |
| Total Mean* | | 0 | |

| | CONTROL SITES | | |
|---|---|---|---|
| | 24 ± 2 hrs | 48 ± 2 hrs | 72 ± 2 hrs |
| Animal ID: 63104 | | | |
| Erythema | 0 0 0 0 0 | 0 0 0 0 0 | 0 0 0 0 0 |
| Edema | 0 0 0 0 0 | 0 0 0 0 0 | 0 0 0 0 0 |
| Total reaction score/observation | 0 | 0 | 0 |
| Total mean* | | 0 | |
| Animal ID: 63045 | | | |
| Erythema | 0 0 0 0 0 | 0 0 0 0 0 | 0 0 0 0 0 |
| Edema | 0 0 0 0 0 | 0 0 0 0 0 | 0 0 0 0 0 |
| Total reaction score/observation | 0 | 0 | 0 |
| Total mean* | | 0 | |
| Animal ID: 63106 | | | |
| Erythema | 0 0 0 0 0 | 0 0 0 0 0 | 0 0 0 0 0 |
| Edema | 0 0 0 0 0 | 0 0 0 0 0 | 0 0 0 0 0 |
| Total reaction score/observation | 0 | 0 | 0 |
| Total Mean* | | 0 | |

*Total mean = total reaction scores/15. Means are rounded to one decimal place.

Interpretation of Results:

Test overall mean score (Total means for all three animals divided by three): 0/3=0

Control overall mean score (Total means for all animals divided by three): 0/3=0

Final test score (The difference between Test overall mean score and Control overall mean score): 0−0=0

TABLE 9

Reaction scores (OIL extract)

| | TEST SITES | | |
|---|---|---|---|
| | 24 ± 2 hrs | 48 ± 2 hrs | 72 ± 2 hrs |
| Animal ID: 63104 | | | |
| Erythema | 1 1 1 1 1 | 1 1 1 1 1 | 1 1 1 1 1 |
| Edema | 0 0 0 0 0 | 0 0 0 0 0 | 0 0 0 0 0 |
| Total reaction score/observation | 5 | 5 | 5 |
| Total Mean* | | 1.0 | |

TABLE 9-continued

Reaction scores (OIL extract)

Animal ID: 63045

| | | | | | | | | | | | | | | | |
|---|---|---|---|---|---|---|---|---|---|---|---|---|---|---|---|
| Erythema | 1 | 1 | 1 | 1 | 1 | 1 | 1 | 1 | 1 | 1 | 1 | 1 | 1 | 1 | 1 |
| Edema | 0 | 0 | 0 | 0 | 0 | 0 | 0 | 0 | 0 | 0 | 0 | 0 | 0 | 0 | 0 |
| Total reaction score/observation | | 5 | | | | | | 5 | | | | | 5 | | |
| Total Mean* | | | | | | | | 1.0 | | | | | | | |

Animal ID: 63106

| | | | | | | | | | | | | | | | |
|---|---|---|---|---|---|---|---|---|---|---|---|---|---|---|---|
| Erythema | 1 | 1 | 1 | 1 | 1 | 1 | 1 | 1 | 1 | 1 | ! | 1 | 1 | 1 | 1 |
| Edema | 0 | 0 | 0 | 0 | 0 | 0 | 0 | 0 | 0 | 0 | 0 | 0 | 0 | 0 | 0 |
| Total reaction score/observation | | 5 | | | | | | 5 | | | | | 5 | | |
| Total Mean* | | | | | | | | 1.0 | | | | | | | |

CONTROL SITES

| | 24 ± 2 hrs | 48 ± 2 hrs | 72 ± 2 hrs |
|---|---|---|---|

Animal ID: 63104

| | | | | | | | | | | | | | | | |
|---|---|---|---|---|---|---|---|---|---|---|---|---|---|---|---|
| Erythema | 1 | 1 | 1 | 1 | 1 | 1 | 1 | 1 | 1 | 1 | 1 | 1 | 1 | 1 | 1 |
| Edema | 0 | 0 | 0 | 0 | 0 | 0 | 0 | 0 | 0 | 0 | 0 | 0 | 0 | 0 | 0 |
| Total reaction score/observation | | 5 | | | | | | 5 | | | | | 5 | | |
| Total Mean* | | | | | | | | 1.0 | | | | | | | |

Animal ID: 63045

| | | | | | | | | | | | | | | | |
|---|---|---|---|---|---|---|---|---|---|---|---|---|---|---|---|
| Erythema | 1 | 1 | 1 | 1 | 1 | 1 | I | 1 | 1 | 1 | 1 | 1 | 1 | 1 | 1 |
| Edema | 0 | 0 | 0 | 0 | 0 | 0 | 0 | 0 | 0 | 0 | 0 | 0 | 0 | 0 | 0 |
| Total reaction score/observation | | 5 | | | | | | 5 | | | | | 5 | | |
| Total Mean* | | | | | | | | 1.0 | | | | | | | |

Animal ID: 63106

| | | | | | | | | | | | | | | | |
|---|---|---|---|---|---|---|---|---|---|---|---|---|---|---|---|
| Erythema | 1 | 1 | 1 | 1 | 1 | 1 | 1 | 1 | 1 | 1 | 1 | 1 | 1 | 1 | 1 |
| Edema | 0 | 0 | 0 | 0 | 0 | 0 | 0 | 0 | 0 | 0 | 0 | 0 | 0 | 0 | 0 |
| Total reaction score/observation | | 5 | | | | | | 5 | | | | | 5 | | |
| Total Mean* | | | | | | | | 1.0 | | | | | | | |

*Total mean = total reaction scores/15. Means are rounded to one decimal place.

Interpretation of Results:

Test overall mean score (Total means for all three animals divided by three): 3.0/3=1.0

Control overall mean score (Total means for all animals divided by three): 3.0/3=1.0

Final test score (The difference between Test overall mean score and Control overall mean score): 1.0−1.0=0

TABLE 10

Positive control reaction scores (Freund's Complete Adjuvant in cottonseed oil)

| | TEST SITES | | |
|---|---|---|---|
| | 24 ± 2 hrs | 48 ± 2 hrs | 72 ± 2 hrs |

Animal ID; 62632

| | | | | | | | | | | | | | | | |
|---|---|---|---|---|---|---|---|---|---|---|---|---|---|---|---|
| Erythema | 3 | 3 | 3 | 3 | 3 | 3 | 3 | 3 | 3 | 3 | 3 | 3 | 3 | 3 | 3 |
| Edema | 4 | 4 | 4 | 4 | 4 | 4 | 4 | 4 | 4 | 4 | 4 | 4 | 4 | 4 | 4 |
| Total reaction score/observation | | 35 | | | | | | 35 | | | | | 35 | | |
| Total Mean* | | | | | | | | 7.0 | | | | | | | |

Animal ID: 62608

| | | | | | | | | | | | | | | | |
|---|---|---|---|---|---|---|---|---|---|---|---|---|---|---|---|
| Erythema | 3 | 3 | 3 | 3 | 3 | 3 | 3 | 3 | 3 | 3 | 4 | 4 | 4 | 4 | 4 |
| Edema | 4 | 4 | 4 | 4 | 4 | 4 | 4 | 4 | 4 | 4 | 4 | 4 | 4 | 4 | 4 |
| Total reaction score/observation | | 35 | | | | | | 35 | | | | | 40 | | |
| Total Mean* | | | | | | | | 7.3 | | | | | | | |

TABLE 10-continued

Positive control reaction scores (Freund's Complete Adjuvant in cottonseed oil)

Animal ID: 62614

| | | | | | | | | | | | | | | | |
|---|---|---|---|---|---|---|---|---|---|---|---|---|---|---|---|
| Erythema | 2 | 2 | 2 | 2 | 2 | 1 | 1 | 1 | 1 | 1 | 2 | 2 | 2 | 2 | 2 |
| Edema | 4 | 4 | 4 | 4 | 4 | 3 | 3 | 3 | 3 | 3 | 3 | 3 | 3 | 3 | 3 |
| Total reaction score/observation | | | 30 | | | | | 20 | | | | | 25 | | |
| Total Mean* | | | | | | | | 5.0 | | | | | | | |

| | CONTROL SITES | | |
|---|---|---|---|
| | 24 ± 2 hrs | 48 ± 2 hrs | 72 ± 2 hrs |

Animal ID: 62632

| | | | | | | | | | | | | | | | |
|---|---|---|---|---|---|---|---|---|---|---|---|---|---|---|---|
| Erythema | 1 | 1 | 1 | 1 | 1 | 1 | 1 | 1 | 1 | 1 | 1 | 1 | 1 | 1 | 1 |
| Edema | 0 | 0 | 0 | 0 | 0 | 0 | 0 | 0 | 0 | 0 | 0 | 0 | 0 | 0 | 0 |
| Total reaction score/observation | | | 5 | | | | | 5 | | | | | 5 | | |
| Total Mean* | | | | | | | | 1.0 | | | | | | | |

Animal ID: 62608

| | | | | | | | | | | | | | | | |
|---|---|---|---|---|---|---|---|---|---|---|---|---|---|---|---|
| Erythema | 1 | 1 | 1 | 1 | 1 | 1 | 1 | 1 | 1 | 1 | 1 | 1 | 1 | 1 | 1 |
| Edema | 0 | 0 | 0 | 0 | 0 | 0 | 0 | 0 | 0 | 0 | 0 | 0 | 0 | 0 | 0 |
| Total reaction score/observation | | | 5 | | | | | 5 | | | | | 5 | | |
| Total Mean* | | | | | | | | 1.0 | | | | | | | |

Animal ID: 62614

| | | | | | | | | | | | | | | | |
|---|---|---|---|---|---|---|---|---|---|---|---|---|---|---|---|
| Erythema | 1 | 1 | 1 | 1 | 1 | 1 | 1 | 1 | 1 | 1 | 1 | 1 | 1 | 1 | 1 |
| Edema | 0 | 0 | 0 | 0 | 0 | 0 | 0 | 0 | 0 | 0 | 0 | 0 | 0 | 0 | 0 |
| Total reaction score/observation | | | 5 | | | | | 5 | | | | | 5 | | |
| Total Mean* | | | | | | | | 1.0 | | | | | | | |

*Total mean = total reaction scores/15. Means are rounded to one decimal place.

Interpretation of Results:
Test overall mean score (Total means for all three animals divided by three): 19.3/3=6.4
Control overall mean score (Total means for all animals divided by three): 3.0/3=1.0
Final test score (The difference between Test overall mean score and Control overall mean score): 6.4–1.0=5.4

TABLE 11

Average reaction scores at each observation period

| Extract | Observation period | Average test score | Average control score | Difference |
|---|---|---|---|---|
| SCI | 24 Hr | 0 | 0 | 0 |
| | 48 Hr | 0 | 0 | 0 |
| | 72 Hr | 0 | 0 | 0 |
| OIL* | 24 Hr | 1.0 | 1.0 | 0 |
| | 48 Hr | 1.0 | 1.0 | o |
| | 72 Hr | 1.0 | 1.0 | 0 |
| Positive control (Freund's adjuvant) | 24 Hr | 6.7 | 1.0 | 5.7 |
| | 48 Hr | 6.0 | 1.0 | 5.0 |
| | 72 Hr | 6.7 | 1.0 | 5.7 |

*Intradermal injection of oil frequently elicits some inflammatory response.
Means are rounded to one decimal place.

All animals remained healthy throughout the test period. The individual irritation scores are presented in Tables 8 and 9. The differences between the overall mean scores for RSF composite and controls using SCI and OIL as extraction media were less than 1.0. Based on erythema and edema scores shown below, no irritation was noted when RSF composite extract injection sites were compared to the control injection sites. Injection of the rabbits with the RSF composite extracts, both in SCI and OIL, did not result in observable negative intracutaneous (intradermal) reactions.

For the SCI extract, the overall mean score for the test was 0, the overall mean score for the control was 0, and the difference between the overall mean scores was 0. For the OIL extract, the overall mean score for the test was 1.0, the overall mean score for the control was 1.0, and the difference between the overall mean scores was 0. The average reaction scores at each observation period for both SCI and OIL are presented in Table 11. The differences between average test scores and average control scores were less than 1.0 at all observation time points.

The susceptibility of the rabbits to a known irritating agent (i.e., the positive control, Freund's Complete Adjuvant in cottonseed oil) was established in a prior positive control study (see Table 10). In this study, the overall mean score for the positive control was 6.4, the overall mean score for the control was 1.0, and the difference between the overall mean scores was 5.4. The differences between average positive control scores and average control scores were greater than 1.0 at all observation periods thus confirming that the rabbits were able to demonstrate detectable skin irritation following injection of an irritating substance.

INCORPORATION BY REFERENCE

The entire contents of all patents, published patent applications and other references cited herein are hereby expressly incorporated herein in their entireties by reference.

EQUIVALENTS

Those skilled in the art will recognize, or be able to ascertain using no more than routine experimentation, numerous equivalents to the specific procedures described herein. Such equivalents were considered to be within the scope of this invention and are covered by the following claims. Moreover, any numerical or alphabetical ranges provided herein are intended to include both the upper and lower value of those ranges. In addition, any listing or grouping is intended, at least in one embodiment, to represent a shorthand or convenient manner of listing independent embodiments; as such, each member of the list should be considered a separate embodiment.

What is claimed is:

1. A tissue separation barrier system for preventing the abnormal union of two or more tissues comprising a single layer anti-adhesion silicone polymer wherein the single layer anti-adhesion silicone polymer is engineered to be implantable between two or more tissues and with sufficient flexibility to allow for ease of movement of said tissues.

2. The tissue separation barrier system of claim 1, wherein the single layer anti-adhesion silicone polymer is engineered to be implantable between two or more tissues in a subject.

3. The tissue separation barrier system of claim 1, wherein the anti-adhesion silicone polymer comprises a reinforced silicone flex (RSF) composite, wherein said RSF composite is a two part composite system formed by the curing of a homogenized mixture of a Part A siloxane with a Part B siloxane and about 20% reinforcing material; and wherein:
    Part A siloxane comprises reinforced dimethyl methylvinyl siloxane, and
    Part B siloxane comprises reinforced dimethyl methylhydrogen siloxane.

4. The tissue separation barrier system of claim 3, wherein Part A and Part B are combined in a ratio of about 11.5 Part A siloxane to 1 Part B siloxane in a weight/weight ratio to form the RSF composite.

5. The tissue separation barrier system of claim 3, wherein said reinforcing material is silica.

6. The tissue separation barrier system of claim 1, wherein the single layer anti-adhesion silicone polymer is engineered to be functionally characterized by exhibiting
    a hardness of about 27 to about 33 on Shore A durometer;
    a tensile strength of greater than or equal to about 600 psi;
    a tear strength of about 100 ppi;
    an elongation limit of greater than or equal to about 350%; and
    a linear shrinkage of about 2%.

7. The tissue separation barrier system of claim 1, wherein the single layer anti-adhesion silicone polymer is shapeable via mold, or transformable via shear or cutting processes into any three dimensional form of a size, shape and thickness sufficient to separate tissues.

8. The tissue separation barrier system of claim 1, wherein the single layer anti-adhesion silicone polymer is removable.

9. The tissue separation barrier system of claim 1, wherein the single layer anti-adhesion silicone polymer is suitable for permanent implantation.

10. A reinforced silicone flex (RSF) composite, wherein said RSF composite is a two part composite system formed by the curing of a homogenized mixture of a Part A siloxane with a Part B siloxane and about 20% reinforcing material; and wherein:
    Part A siloxane comprises reinforced dimethyl methylvinyl siloxane, and
    Part B siloxane comprises reinforced dimethyl methylhydrogen siloxane.

11. The RSF composite of claim 10, wherein Part A siloxane and Part B siloxane are combined in a ratio of about 11.5 Part A siloxane to 1 Part B siloxane in a weight/weight ratio to form the RSF composite.

12. The RSF composite of claim 11, wherein said reinforcing material is silica.

13. A method of separating two or more tissues comprising implantation of a single layer anti-adhesion silicone polymer of the tissue separation barrier system of claim 1 between two or more tissues, wherein said single layer anti-adhesion silicone polymer is engineered with sufficient flexibility to allow for ease of movement of said tissues,
    such that said tissues remain separated until removal of said single layer anti-adhesion silicone polymer.

14. A method of preventing the abnormal union of any two or more tissues comprising implantation of a single layer anti-adhesion silicone polymer of the tissue separation barrier system of claim 1 between two or more tissues, wherein said single layer anti-adhesion silicone polymer is engineered with sufficient flexibility to allow for ease of movement of said tissues,
    such that the abnormal union of said tissues is prevented until removal of said single layer anti-adhesion silicone polymer.

15. The method of preventing the abnormal union of tissues of claim 14, wherein the method prevents the formation of adhesions between said tissues.

16. A method of protecting a sub-epidermal wound comprising implantation of a single layer anti-adhesion silicone polymer of the tissue separation barrier system of claim 1 between two or more tissues, wherein at least one of said tissues requires protection as a result of a wound, wherein said single layer anti-adhesion silicone polymer is engineered with sufficient flexibility to allow for ease of movement of said tissues,
    such that said sub-epidermal wound remains protected until removal of said single layer anti-adhesion silicone polymer.

17. The method of protecting of claim 16, wherein the implantation protects a sub-epidermal wound from tissues selected from the group consisting of connective tissue, muscle tissue, nervous tissue, epithelial tissue, and any combination thereof.

18. A method of manufacturing a single layer anti-adhesion silicone polymer of claim 1 comprising the steps of:
    placing a mixture of a Part A siloxane and a Part B siloxane into a container, wherein the Part A siloxane comprises reinforced dimethyl methylvinyl siloxane, and the Part B siloxane comprises reinforced dimethyl methylhydrogen siloxane, and combined comprise about 20% reinforcing material;
    subjecting the mixture to a pre-injection homogenization process;
    injecting the pre-injection processed mixture into a mold;
    curing the molded mixture in an oven;
    cooling the molded mixture to room temperature; and
    demolding the cured mixture,
    thus forming a single layer anti-adhesion silicone polymer of claim 1.

19. The manufacturing method of claim 18, wherein Part A siloxane and Part B siloxane are combined in a weight/weight ratio of about 11.5 Part A siloxane to 1 Part B siloxane.

20. The manufacturing method of claim 18, wherein said reinforcing material is silica.

* * * * *